(12) United States Patent
Yamaguchi et al.

(10) Patent No.: US 10,332,647 B2
(45) Date of Patent: Jun. 25, 2019

(54) LIGHT SOURCE DEVICE FOR COLLIMATOR

(71) Applicant: Shimadzu Corporation, Kyoto (JP)

(72) Inventors: Narumi Yamaguchi, Kyoto (JP); Koji Watadani, Kyoto (JP); Satoshi Yamaguchi, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 203 days.

(21) Appl. No.: 15/486,842

(22) Filed: Apr. 13, 2017

(65) Prior Publication Data

US 2018/0299099 A1 Oct. 18, 2018

(51) Int. Cl.
*G02B 19/00* (2006.01)
*G21K 1/04* (2006.01)
*A61B 6/08* (2006.01)
*G01N 23/04* (2018.01)

(52) U.S. Cl.
CPC ............... *G21K 1/046* (2013.01); *A61B 6/08* (2013.01); *G01N 23/04* (2013.01)

(58) Field of Classification Search
CPC ..... A61B 6/4064; A61B 6/4085; A61B 6/542; A61B 6/08; G02B 6/262; G02B 6/264; G02B 6/32; G02B 3/08; G02B 19/0028; G02B 19/0042; G02B 27/30; F21K 9/50; F21K 9/30; F21V 5/04; F21V 19/001; F21V 29/004; F21V 21/14; F21V 29/2212; F21V 29/773; F21V 29/08; G01N 2223/323; G01N 2223/316

See application file for complete search history.

(56) References Cited

U.S. PATENT DOCUMENTS

| | | | |
|---|---|---|---|
| 2004/0131157 A1* | 7/2004 | Stevanovic | A61B 6/08 378/145 |
| 2018/0129027 A1* | 5/2018 | Jurik | F21S 10/007 |

* cited by examiner

*Primary Examiner* — Don K Wong
(74) *Attorney, Agent, or Firm* — Muir Patent Law, PLLC

(57) ABSTRACT

Provided is a light source device for a collimator capable of improving an illuminance ratio in an inside of a visible light's radiation field to an outside thereof. The light source device for a collimator includes an LED with a light emitting portion that irradiates visible light and a visible light guide member. The visible light guide member may have a main body, a spacer, and a base. In the main body, a through-hole of a truncated conical shape is formed. The through-hole of a truncated cone shape forms a first opening at a first surface of the main body on a side of the LED and a second opening a second surface of the main body opposite to the first surface. The first opening may be smaller than the second opening. The conical surface of the through-hole having the truncated conical shape is formed as a mirror surface which reflects the visible light irradiated from the LED with high reflectance.

7 Claims, 6 Drawing Sheets

LIGHT SOURCE DEVICE FOR COLLIMATOR

TECHNICAL FIELD

The present invention relates to a light source device for a collimator used for displaying an X-ray radiation field formed by a collimator with visible light in an X-ray equipment.

BACKGROUND TECHNIQUE

In such an X-ray equipment, between the X-ray tube and the X-ray detector, for the purpose of regulating the X-ray radiation field, which is an irradiation range of the X-ray irradiated from the X-ray tube with respect to a subject, a collimator which is an X-ray diaphragm mechanism including a plurality of collimator leaves arranged in an openable and closable manner in the radiation range of the X-ray irradiated from the X-ray tube is installed. When adjusting the X-ray radiation field to be irradiated from the X-ray tube toward the subject using the collimator, a visible light source called a collimator lamp installed in the collimator on the opposite side of the object is turned on to form a radiation field of visible light so that the radiation field of the visible light can be visually recognized. Thus, the X-ray radiation field to be adjusted by the collimator mechanism is confirmed (see Japanese Patent Application Publication No. 2001-70292 (hereinafter referred to as "Patent Document 1"); and Japanese Patent Application Publication No. 2013-215495 (hereinafter referred to as "Patent Document 2").

As a visible light source for such a collimator, conventionally, a halogen lamp has been used. A halogen lamp has a problem that the power consumption is large. In addition, there also is a problem that a halogen lamp is relatively short in lifetime, which requires regular replacement.

For this reason, a light source device for a collimator has been proposed in which an LED for irradiating visible light is used as a light source (see Japanese Patent Application Publication No. 2004-209259 (hereinafter referred to as "Patent Document 3")). In the light source device for a collimator described in Patent Document 3, in order to improve the illuminance ratio (edge contrast) between the radiation field by the visible light and the outer circumference region of the radiation field, it is configured such that LEDs are arranged inside a cone of a compound parabolic condenser (CPC) shape.

In the light source device for a collimator described in the aforementioned Patent Document 3, since all of visible lights irradiated from the LEDs are condensed by the reflecting surface, the illuminance in the visible light radiation field is improved. However, visible lights directed in all directions are condensed, which in turn causes a difficulty in obtaining an illuminance ratio exceeding a certain level. In the light source device for a collimator described in Patent Document 3, as described in Patent Document 3, the illuminance ratio between a region inside from the edge of the radiation field of the visible light by 3 mm and a region outside from the edge of the radiation field of the visible light by 3 mm is only about 1.458 or 1.923.

SUMMARY OF THE INVENTION

The present invention addresses one or more of the aforementioned problems, providing a light source device for a collimator capable of further improving an illuminance ratio between an inside of a radiation flied of visible light and an outside thereof, as well as related methods of operating such collimator.

In some examples, a light source device for a collimator used to display an X-ray radiation field formed by a collimator with visible light in an X-ray equipment, includes an LED for irradiating visible light, and a visible light guide member configured to condense the visible light irradiated from the LED after limiting a radiation range. The visible light guide member is provided with a through-hole having a first opening formed on an LED side, a second opening formed on an opposite side of the LED concentrically with the first opening, the second opening having an area larger than an area of the first opening, and a side surface connecting the first opening and the second opening. The side surface of the through-hole is formed in a mirror surface reflecting the visible light. The area of the first opening of the through-hole is smaller than an area of a light emitting surface of the LED.

In some examples, the through-hole has a frustum shape in which the first opening is a top surface, the second opening is a bottom surface, and the side surface is a conical surface or pyramidal surface.

In some examples, a light emitting surface of the LED and a surface of a region of the visible light guide member in which an LED side opening is formed are separated by a predetermined distance.

In some examples, the visible light guide member has a light-tight structure that prevents visible light irradiated from the LED from exiting from a region other than the through-hole to an outside.

In some examples, the visible light guide member is made of metal, and the conical surface or pyramidal surface of the through-hole is mirror-finished.

According to some examples, by the function of the visible light guide member which condenses the visible light irradiated from the LED after limiting the radiation range, it becomes possible to make the illuminance ratio between the inner and outer regions of the radiation field of the visible light extremely high. This makes it possible to more accurately recognize the radiation field of the visible light, that is, the X-ray radiation field.

Providing a predetermined distance between the light emitting surface of the LED and the surface of the visible light guide member on the side in which the LED side opening is formed, may make the illuminance ratio between the inner and outer regions of the radiation field of the visible light extremely high.

When the visible light guide member has a light-tight structure that prevents the visible light from exiting outside the region other than the through-hole, it is possible to prevent the phenomenon that the stray light irradiated from the LED reaches the vicinity of the radiation field of the visible light and lower the illuminance ratio.

When the visible light guide member is made of metal, even in cases where a large heat generation occurs from the LED using a high power LED, it is possible to prevent the visible light guide member from being deteriorated and to release the heat promptly to the outside.

BRIEF DESCRIPTION OF THE DRAWINGS

Embodiments of the present invention are shown by way of example, and not limitation, in the accompanying drawings.

EMBODIMENTS FOR CARRYING OUT THE INVENTION

In the following paragraphs, some embodiments of the present invention will be described by way of example and not limitation. It should be understood based on this disclosure that various other modifications can be made by those in the art based on these illustrated embodiments.

Figure 1:
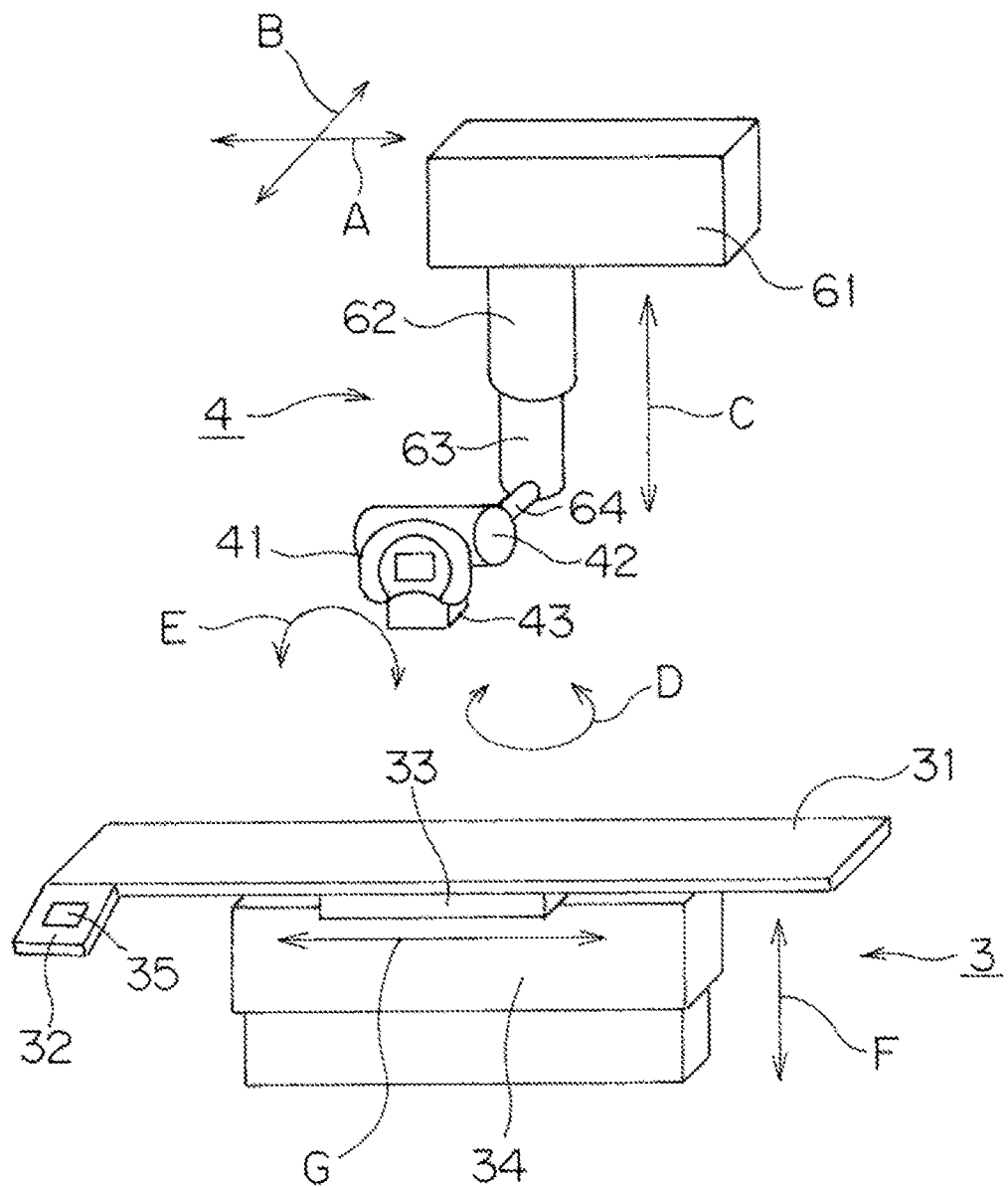
FIG. 1 is a schematic diagram of an X-ray equipment to which a light source device 10 for a collimator according to the present invention is applied.

Hereinafter, embodiments of the present invention will be described with reference to the attached drawings. FIG. 1 is a schematic diagram of an X-ray equipment to which a light source device 10 for a collimator according to the present invention is applied.

This X-ray equipment is equipped with a radiographic stand 3 and an X-ray irradiation unit 4 installed in an X-ray radiographing room. The radiographic stand 3 is equipped with a top board 31 on which a subject is placed, an operation panel 32 having a display portion 35 configured by a touch panel type liquid crystal display, and a Bucky unit 33 in which an X-ray detector, such as, e.g., a flat panel detector, is accommodated therein, and a lifting unit 34 configured to move up and down the top board 31 and the Bucky unit 33. The Bucky unit 33 is horizontally movable in the G direction shown in FIG. 1. Furthermore, the Bucky unit 33 is configured so as to be moved upward and downward in the F direction shown in FIG. 1 together with the top board 31.

The X-ray irradiation unit 4 is equipped with a support portion 61 configured to be movable in the directions A and B orthogonal with each other with respect to the ceiling of the X-ray imaging room, a hanging portion 62 extending downward from the support portion 61, a moving portion 63 configured to move up and down in the C direction with respect to the hanging portion 62 and rotate in the D direction, a support shaft 64 pivotally supported at the lower end portion of the moving portion 63 and configured to integrally rotate the operation unit 41, the X-ray tube 42, and the collimator 43 in the E direction. Therefore, the X-ray tube 42 is movable in the directions A, B, C, D, and E shown in FIG. 1 together with the operation unit 41 and the collimator 43.

Figure 2:
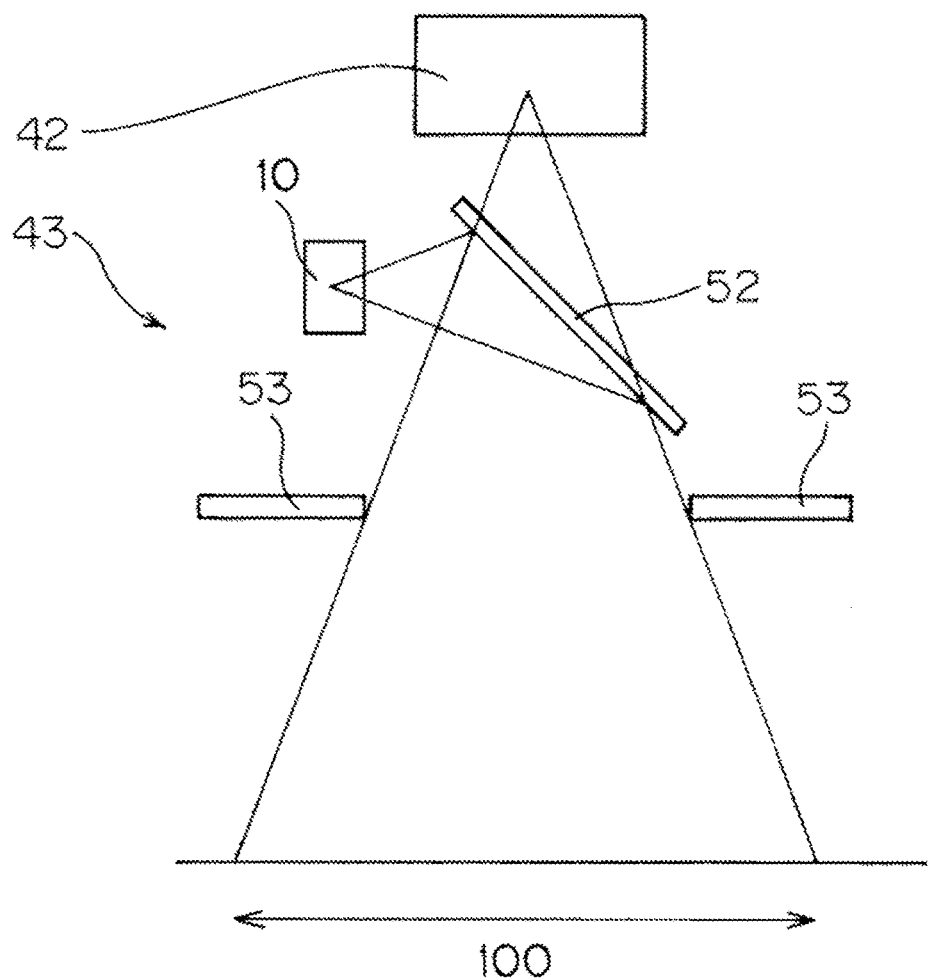
FIG. 2 is a schematic diagram of a collimator 43.

FIG. 2 is a schematic diagram of the collimator 43.

The collimator 43 is equipped with four collimator leaves 53 for limiting the radiation field of the X-ray irradiated from the X-ray tube 42. In this figure, only two collimator leaves 53 are illustrated, but in reality, a rectangular X-ray radiation field is formed by four collimator leaves 53. In this figure, the radiation field of the X-ray and the radiation field of the visible light which will described later are indicated by the reference numeral 100. The collimator 43 is provided with a light source device 10 for a collimator according to the present invention which irradiates visible light for making the field of X-ray radiation visible. The visible light irradiated from the light source device 10 is reflected by the mirror 52 toward and through an opening formed by the collimator leaves through which the X-ray can pass, so that a rectangular visible light radiation field is formed by the four collimator leaves 53. The size of the radiation field of this visible light is the same as the size of the X-ray radiation field. Thus, the operator can confirm the X-ray radiation field by confirming the radiation field of the visible light.

Figure 3:
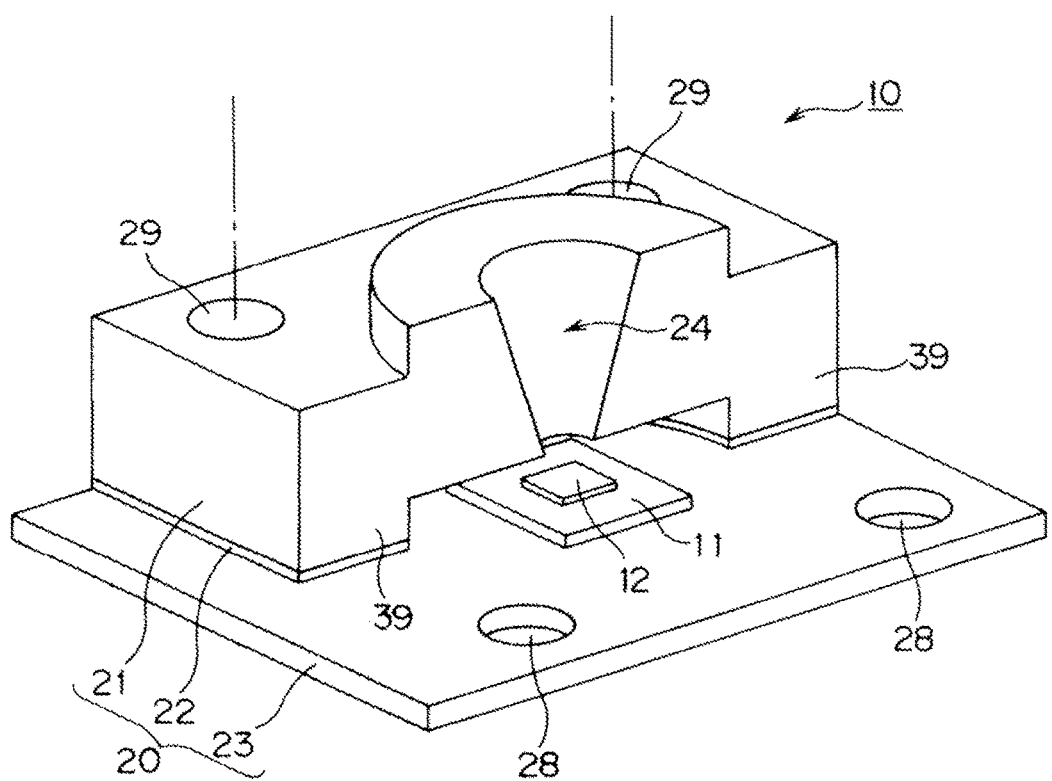
FIG. 3 is a perspective view of the light source device 10 for a collimator.
Figure 4:
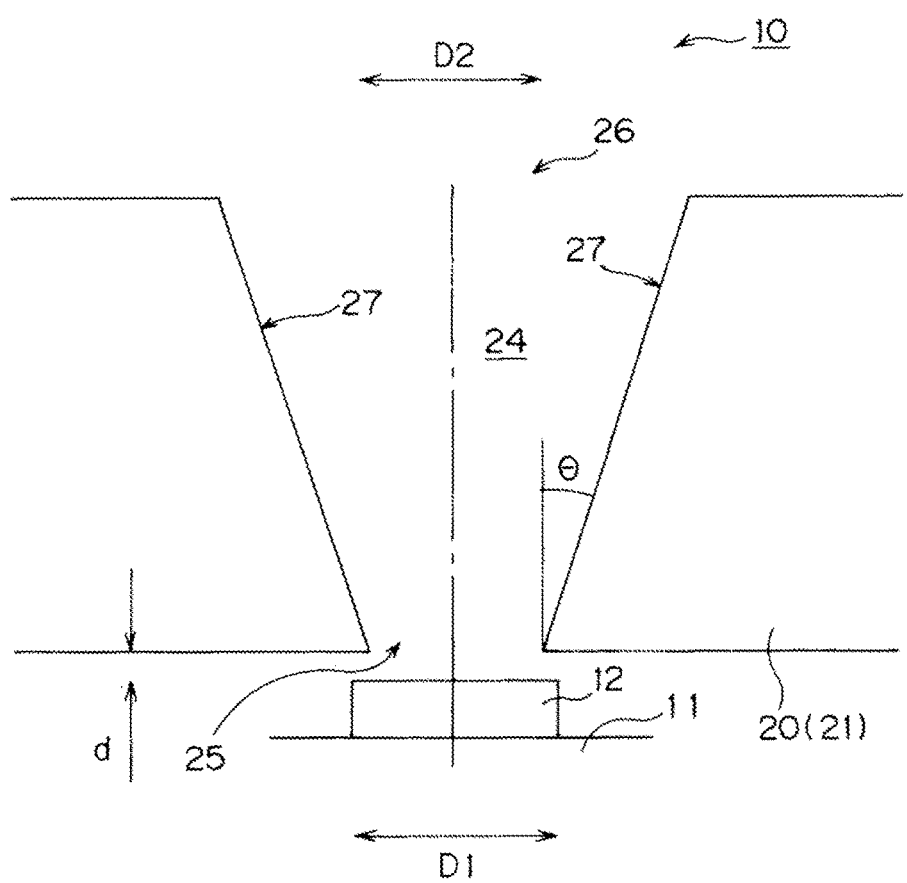
FIG. 4 is an enlarged cross-sectional view showing the vicinity of a through-hole 24 of the visible light guide member 20 of the light source device 10 for a collimator.

Next, the configuration of the light source device 10 for a collimator according to the present invention will be described. FIG. 3 is a perspective view of the light source device 10 for a collimator. FIG. 4 is an enlarged cross-sectional view of the vicinity of the through-hole 24 of the visible light guide member 20 of the light source device 10 for a collimator. In FIG. 3, in order to illustrate the internal structure of the visible light guide member 20, this figure illustrates a state in which the visible light guide member 20 is cut in half.

This light source device 10 for a collimator includes an LED (Light Emitting Diode) 11 provided with a light emitting portion 12 for irradiating visible light. The light emitting portion 12 of the LED 11 may be provided with a single light radiation range (e.g., a constant intensity across the light emitting surface of the light emitting portion 12), a plurality of light radiation ranges (e.g., varying intensity of visible light across the light emitting surface of the light emitting portion 12), and/or a plurality of light emitting elements arranged in a row.

The light source device 10 for a collimator is equipped with the visible light guide member 20 that guides the visible light irradiated from the LED 11 after limiting the radiation range. This visible light guide member 20 is configured by a main body 21, a spacer 22, and a base 23 made of metal. The main body 21, spacer 22, and base 23 are fixed to each other by screws or the like (not illustrated) by utilizing the fastening holes 29 formed in the main body 21, the fastening holes (not illustrated) formed in the spacer 22, and the fastening holes 28 formed in the base 23.

In the main body 21 of the visible light guide member 20, a through-hole 24 having a truncated conical shape is bored. The through-hole 24 having a truncated cone shape forms a first opening 25 at the top surface of the visible light guide member 20 (the surface facing the side of the LED 11 and shown facing downward with respect to the illustration of FIG. 3) and forms a second opening 26 at a bottom surface of the visible light guide member 20 (on the side opposite to the LED 11 and shown facing upward with respect to the illustration of FIG. 3). The conical surface (side surface) 27 of the through-hole 24 having a truncated conical shape is a reflective surface (e.g., a mirror surface) that reflects the visible light irradiated from the LED 11 with high reflectance. The area of the opening 25 of the through-hole 24 on the side of the LED 11 is smaller than the area of the light emitting surface of the light emitting portion 12 of the LED 11.

As shown in FIG. 3, the light emitting portion 12 of the LED 11 has a rectangular shape with respect to a plan view. The length of one side of the light emitting portion 12 is D1 as shown in FIG. 4. On the other hand, the diameter D2 of the opening 25 formed in the main body 21 of the visible light guide member 20 on the side of the LED 11 is set to be smaller than the length D1 of the one side of the light emitting portion 12 of the LED 11. Therefore, the area of the opening 25 of the through-hole 24 on the side of the LED 11 is smaller than the area of the light emitting surface of the light emitting portion 12 of the LED 11. The length of the sides perpendicular to the one side of the light emitting diode portion 12 may be equal to or greater than D1.

Also, as shown in FIG. 4, the angle formed by the conical surface 27 of the through-hole 24 having a truncated conical shape and the vertical direction is θ. The light emitting surface which is an upper surface of the light emitting portion 12 of the LED 11 and the surface (lower surface) of the LED 11 side region of the main body 21 of the visible light guide member 20 where the opening 25 is formed are separated by a predetermined distance "d".

A plurality of spacers 22' (which may have different thicknesses) may be provided, one or more of which is selected for the spacer 22 in the visible light guide member 20. Therefore, by appropriately selecting the thickness and the number of spacers 22, it is possible to change the distance "d" between the light emitting surface which is the upper surface of the light emitting portion 12 of the LED 11 and the surface of the LED 11 side region of the main body 21 of the visible light guide member 20 where the opening 25 is formed. When this distance "d" is increased, even if the area of the opening 25 of the through-hole 24 of the visible light guide member 20 on the LED 11 side is increased, it is possible to increase the illuminance ratio in the inner and outer regions of the radiation field of the visible light. However, it is also possible to have no distance "d" (or a distance "d" of zero) such as when the area of the opening 25 of the through-hole 24 of the visible light guide member 20 on the LED 11 side is reduced sufficiently.

In the region of the visible light guide member 20 facing the LED 11, a recess is formed by the leg part 39 and the spacer 22 of the main body 21, and the LED 11 is accommodated in this recess, being mounted on base 23. Therefore, the LED 11 is surrounded by the main body 21, the spacer 22, and the base 23 of the visible light guide member 20. As a result, the visible light guide member 20 has a light-tight structure that prevents the visible light irradiated from the light emitting portion 12 of the LED 11 from exiting the light source 10 other than the through-hole 24.

The main body 21 of the visible light guide member 20 is manufactured by pressing an aluminum (Al) material. Then, the conical surface 27 of the through-hole 24 of the main body 21 is formed in a mirror surface in which the surface roughness is sufficiently fine and smooth and the reflectance of the visible light is about 80% by an ironing drawing process (or by an ironing process) at the time of the press working.

In the light source device 10 for a collimator having the aforementioned configuration, the area of the opening 25 of the through-hole 24 on the side of the LED 11 is smaller than the area of the light emitting surface of the light emitting portion 12 of the LED 11. The visible light irradiated from the light emitting portion 12 of the LED 11 enters the through-hole 24 from the opening 25 only from the central section of the light emitting portion 12 where the light emission intensity is highest. In this way, by limiting the radiation range of the visible light taken into the visible light guide member 20 among the visible light irradiated from the light emitting portion 12 of the LED 11 to a small region, it is possible to increase the illuminance ratio of the inside regions to outside regions of the radiation field of the visible light.

Figure 5:
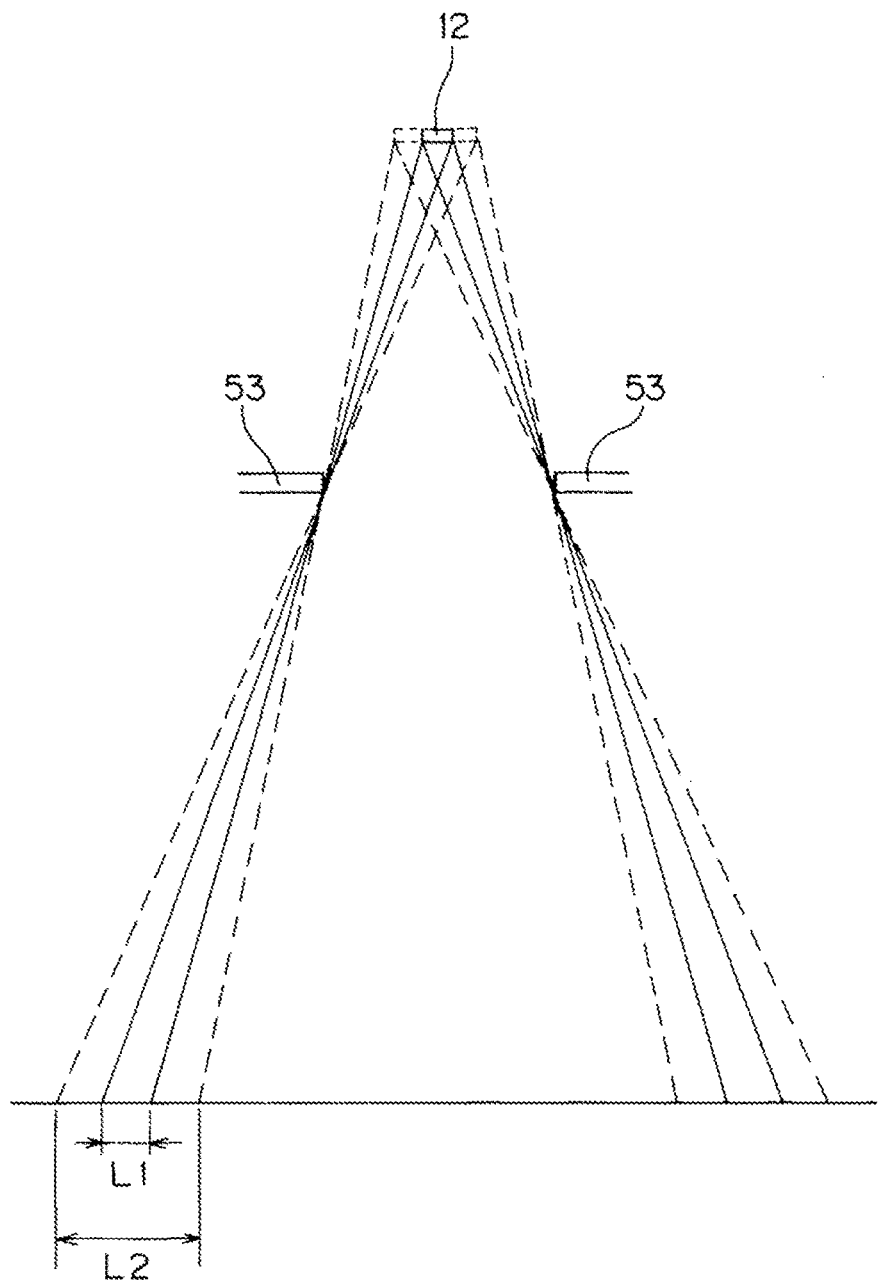
FIG. 5 is a schematic diagram showing a state in which the visible light irradiated from the light emitting portion 12 of the LED 11 is blocked by the collimator leaves 53 to form a radiation field of the radiation light.

FIG. 5 is a schematic diagram showing a state in which the visible light irradiated from the light emitting portion 12 of the LED 11 is blocked by the collimator leaves 53 to form the radiation field of the visible light.

As shown by the solid line in this figure, when the region of the visible light irradiated from the light emitting portion 12 and entering the through-hole 24 is reduced, the range of the visible light emitted from both ends of the region and intercepted by the collimator leaves 53 becomes L1. On the other hand, as shown by the dashed line in this figure, when the region of the visible light irradiated from the light emitting portion 12 and entering the through-hole 24 is increased, the range of the visible light emitted from both ends of the region and intercepted by the collimator leaves 53 becomes L2 larger than L1. The ranges L1 and L2 are regions where the shadow of the collimator leaves 53 is blurred at the edge of the radiation field of the visible light, and as the width of this region increases, the illuminance ratio decreases. As shown in FIG. 5, by reducing the region of the visible light irradiated from the light emitting portion 12 and entering the through-hole 24, it is possible to reduce the region where the edge of the radiation field is blurred, maintaining the illuminance ratio of the to and outside regions of the radiation field of the visible light high.

On the other hand, the visible light irradiated from the light emitting portion 12 of the LED 11 and entering the through-hole 24 via the opening 25 is guided and condensed by being reflected by the conical surface 27 of the through-hole 24 having a truncated cone shape, and forms a radiation field of the visible light. Even in the case of adopting the configuration in which only a part of the visible light irradiated from the light emitting portion 12 of the LED 11 is introduced to the through-hole 24, the visible light irradiated from the light emitting portion 12 of the LED 11 using the reflection at the conical surface 27 can be efficiently guided to the radiation field of the visible light, which increases the illuminance of the radiation field of the visible light. In this case, by setting the angle θ formed by the conical surface 27 of the through-hole 24 having a truncated cone shape and the vertical direction to be about 16 degrees to about 19 degrees, the illuminance of the radiation field of visible light can be maximized.

In the light source device 10 for a collimator having such a configuration, the inventors of the present invention confirmed the following facts through experiments. That is, when it is set such that the distance "d" between the light emitting surface on the upper surface of the light emitting portion 12 of the LED 11 and the surface of the LED side region of the visible light guide member 20 where the opening 25 is formed is 0.4 mm to 0.7 mm and the diameter of the opening 25 is 1.65 mm to 1.85 mm, it is possible to make the illuminance ratio in the region 3 mm inner than the region where the illuminance of the visible light is ¼ of the maximum illuminance of the radiation field of the visible light and the region 3 mm outer than the region where the illuminance of the visible light is ¼ of the maximum illuminance of the radiation field of the visible light in the vicinity of the radiation field of visible light to 4.0 or more.

Further, in the light source device 10 for a collimator, the LED 11 is surrounded by the main body 21, the spacer 22, and the base 23 in the visible light guide member 20. The visible light guide member 20 has a light-tight structure in which the visible light irradiated from the light emitting portion 12 of the LED 11 is prevented from exiting outside the region other than the through-hole 24. Therefore, in the light source device 10 for a collimator, it is possible to prevent the phenomenon that the stray light irradiated from the light emitting portion 12 of the LED 11 reaches the vicinity of the radiation field of the visible light and lowers the illuminance ratio.

Figure 6:
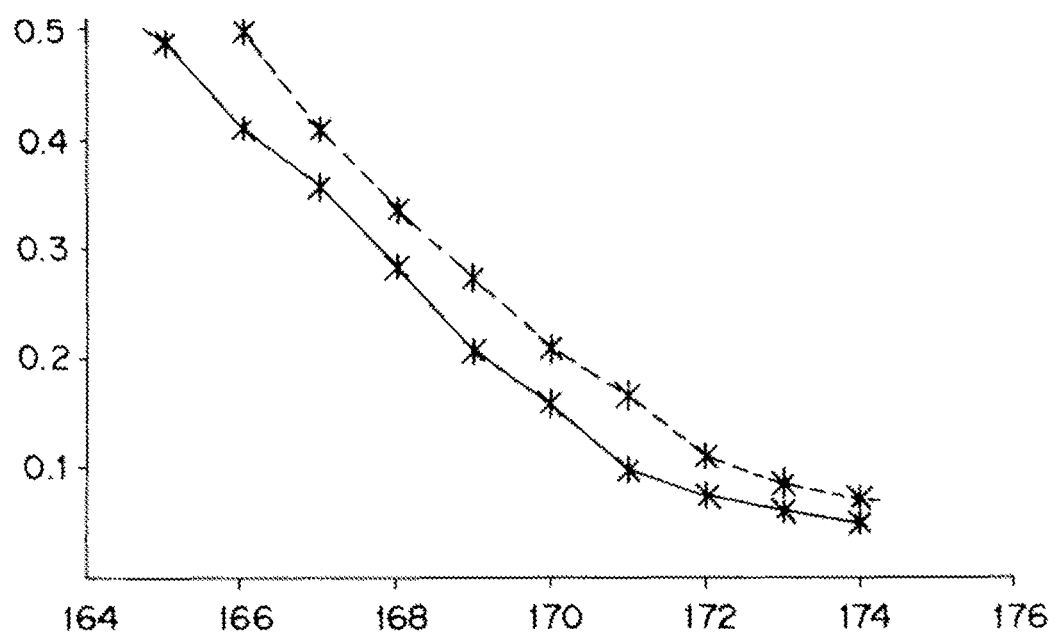
FIG. 6 is a graph comparing the illuminance ratios in the case in which the light source device 10 for a collimator is configured to have a light-tight structure and in the case in which the light source device 10 for a collimator is configured not to have a light-tight structure.

FIG. 6 is a graph comparing the illuminance ratios in the case in which the light source device 10 for a collimator is configured to have a light-tight structure and in the case in which the light source device 10 for a collimator is configured not to have a light-tight structure. In FIG. 6, the horizontal axis shows the distance from the center of the radiation field of the visible light, and the vertical axis shows the illuminance standardized by the maximum illuminance of the region 3 mm outside the region where the illuminance of the visible light is ¼ of the maximum illuminance of the radiation field of visible light. Also in this figure, the solid line shows the case in which the aforementioned light source device 10 for a collimator is applied, and the broken line shows the case in which the region corresponding to the leg part 39 in the main body 21 of the visible light guide member 20 is opened.

As shown in this figure, in the case in which the visible light guide member 20 in the light source device 10 for a collimator has a light-tight structure, compared with the case in which it is configured not to have a light-tight structure, the illuminance of the region 3 mm outside the region in which the illuminance of the visible light is ¼ of the maximum illuminance of the radiation field of the visible light can be reduced, which can make the illuminance ratio in the inner and outer regions of the radiation field of the visible light higher.

In the aforementioned embodiment, a through-hole 24 having a truncated cone shape is adopted, but other frustum shapes, such as, e.g., a polygonal truncated cone, may be adopted. For example, as a shape of the through-hole 24, a truncated quadrangular pyramid corresponding to the rectangular radiation field formed by the collimator leaves 53 may be adopted. Also, it is also possible to adopt a through-hole having a shape other than a truncated cone shape. For example, a through-hole may be adopted having a different shape such as, with respect to a vertical cross section of the main body 21 at the opening 25 and the opening 26 (e.g., a cross section taken at a location and direction as shown in FIG. 4, but with respect to a differently shaped through-hole 24), openings 25 and 26 are connected not by a straight line but by a curve such as a parabola, or by a line including a straight line and a curve.

Further, in the aforementioned embodiment, as the main body 21 of the visible light guide member 20, a member manufactured by pressing an aluminum material is adopted. Thereby, the manufacturing cost of the main body 21 of the visible light guide member 20 can be reduced. In addition, even if heat is generated from the LED 11 by using a high power LED as the LED 11, deterioration does not occur. Further, the main body 21 it has a high thermal conductivity, it is possible to efficiently divert the heat generated from the LED 11. However, instead of aluminum, another metal or alloy having high thermal conductivity may be used, or a reflective film may be deposited on the surface of a shaped or sintered body made of ceramics or the like. In addition, when the heat generation from the LED 11 is small, a reflecting film deposited on the surface of the resin may be used.

It should be understood that the terms and expressions used herein are used for explanation and have no intention to be used to construe in a limited manner, do not eliminate any equivalents of features shown and mentioned herein, and allow various modifications falling within the claimed scope of the present invention.

DESCRIPTION OF REFERENCE SYMBOLS 3 radiographic stand
4 X-ray irradiation unit
10 light source device for a collimator
11 LED
12 light emitting portion
20 visible light guide member
21 main body
22 spacer
23 base
24 through-hole
25 opening
26 opening
27 conical surface
31 top board
33 Bucky unit
39 leg part
42 X-ray tube
43 collimator
52 mirror
53 collimator leaf

The invention claimed is:

1. A light source device for a collimator used to display an X-ray radiation field formed by a collimator with visible light in an X-ray equipment, the light source device comprising:
 a light emitting diode (LED) for irradiating visible light; and
 a visible light guide member configured to block a portion of the visible light irradiated from the LED and to condense a remaining portion of the visible light irradiated from the LED,
 wherein the visible light guide member is provided with a through-hole having a first opening formed at a first surface of the visible light guide member facing the LED, a second opening formed at a second surface of the visible light guide member opposite of the first surface, wherein the first and second opening are centered about a geometric line parallel to the light axis, wherein the second opening has an area larger than an area of the first opening, and wherein the through-hole is defined by a side surface extending between the first opening and the second opening,
 wherein the side surface of the through-hole is formed as a mirror surface to reflect the visible light, and
 wherein the area of the first opening of the through-hole is smaller than an area of a light emitting surface of the LED.

2. The light source device for a collimator as recited in claim 1,
 wherein the through-hole has a frustum shape in which the first opening is a top surface, the second opening is a bottom surface, and the side surface is a conical surface or a pyramidal surface.

3. The light source device for a collimator as recited in claim 2,
 wherein the light emitting surface of the LED and the first surface are separated by a predetermined distance.

4. The light source device for a collimator as recited in claim 1,
 wherein the visible light guide member has a light-tight structure that prevents visible light irradiated from the LED from exiting the visible light guide member other than via the through-hole.

5. The light source device for a collimator as recited in claim 1, wherein the visible light guide member is made of metal, the side surface of the through-hole has a mirror finish, and the side surface is a conical surface or a pyramidal surface.

6. The light source device for a collimator as recited in claim 1, wherein the first and second openings are concentric.

7. The light source device for a collimator as recited in claim 1,
wherein the first opening is a top surface, the second opening is a bottom surface, and the side surface has a linear shape extending from the top surface to the bottom surface when viewed in cross-section.

* * * * *